United States Patent [19]

Barker et al.

[11] 4,335,103

[45] Jun. 15, 1982

[54] MULTIPHASE COSMETIC COMPOSITION

[75] Inventors: Patricia I. M. Barker, Apex; Nathan A. Ziskin; Michael J. Grossfeld, both of Raleigh, all of N.C.

[73] Assignee: Almay, Inc., Apex, N.C.

[21] Appl. No.: 781,573

[22] Filed: Mar. 28, 1977

[51] Int. Cl.$^3$ ............... A61K 7/021; A61K 7/42; A61K 7/48; A61K 7/50

[52] U.S. Cl. .................. 424/59; 424/63; 424/64; 424/65; 424/81; 424/358; 424/365; 424/DIG. 5

[58] Field of Search ............ 424/49, 59, 63, 64, 424/65, 81, 170, 358, 365, DIG. 5

[56] References Cited

U.S. PATENT DOCUMENTS

| | | | |
|---|---|---|---|
| 1,320,855 | 11/1919 | Henderson | 424/DIG. 5 |
| 2,566,722 | 9/1951 | Friedberg | 424/DIG. 5 |
| 2,970,083 | 1/1961 | Bell | 424/DIG. 5 |
| 3,279,999 | 10/1966 | Harrison | 424/DIG. 5 |
| 3,479,429 | 11/1969 | Morshauser | 424/64 |
| 3,980,767 | 9/1976 | Chown | 424/49 X |

OTHER PUBLICATIONS

Carbopol 934, Bulletin, Supp. No. 1, Mar. 1959, B. F. Goodrich Chem. Co., Cleveland, Ohio, 4 pp.
Balsam & Sagarin, Cos., Sci. & Tech., Wiley-Intersci., N.Y., vol. 1, 2nd ed., 1972, pp. 5-24, 201-205.

*Primary Examiner*—Anna P. Fagelson
*Attorney, Agent, or Firm*—Mills and Coats

[57] ABSTRACT

The present invention relates to a multiphase cosmetic composition wherein respective phases throughout the total composition are generally stable, separate, and visually distinct.

Disclosed herein is a duophase cosmetic cleansing cream composition including two generally separate and stable cosmetic compositions intimately mixed to yield a cleansing type composition that may be applied to a subject's face or body in one step, with the composition including a first cleansing cream phase composition comprising the following with each being expressed as a percentage of weight of said cleansing cream phase: an oil making up about 40–65% by weight of the cream phase composition, water making up about 20–50% of the cream phase composition and a thickening agent comprising about 0.25–1.70% by weight of the cream phase composition, and an emulsifier making up about 1.0–9.0% by weight of the cream phase composition; and a gel phase including the following with each being expressed as a percentage of weight of the gel phase: water or water soluble material making up about 80–95% by weight of the gel phase composition, and a thickening agent making up approximately 0.50–4.00% by weight of said gel phase composition. The respective cream and gel phases just set forth above are intimately blended, mixed, or combined in preferably a swirl or marble like type configuration such that the respective phases exist throughout the entire composition as formed by the two combined phases and wherein each respective phase remains generally separate, stable and visually distinct.

15 Claims, No Drawings

MULTIPHASE COSMETIC COMPOSITION

The present invention relates to cosmetic compositions.

BACKGROUND OF THE INVENTION

Cosmetic cleansing creams, toners, astringents, lotions, etc., are, of course, in wide use today. Cleansing creams, for example, are extremely useful in facial and body cleansing, especially to remove make-up, dirt, soil and other undesirable film like dirt that might form about a person's face or body. After cleansing, it is not uncommon that a toner or astringent type composition be applied over the face or the body to generally condition and tone the skin. Obviously the application of make-up, preceded by preparation and followed by cleansing, conditioning, etc., requires time and effort on the part of the subject. While the time and effort for such is worthwhile and tolerable even where meticulous care is exercised and much time consumed, it is, however, apparent that at least some cosmetics could be formulated which would emphasize convenience and yet be completely functional.

SUMMARY OF THE INVENTION

The present invention relates to a multiphase cosmetic composition wherein respective composition phases are combined to form a continuous multiphase cosmetic composition with each respective phase comprising the total composition being generally stable, separate and visually distinct. A particular embodiment of the multiphase cosmetic composition disclosed herein presents a dual phase or duophase cleansing cream composition that is basically comprised of two phases—one phase being an emulsified cream composition while the other phase is referred to as a gel phase. In the case of this duophase cosmetic cleansing cream composition, the cream phase functions as a cleanser while the gel phase functions as a toner like conditioner. With respect to the duophase cosmetic cleansing cream composition, the respective cream and gel phases are combined preferably in a swirl like or marble like pattern within a container such that the cream and gel phases are generally stable, separate and visually distinct with the particular phases being so dispensed and combined within the total composition so that in gathering a modest application about the finger tips, the gathered application will generally include both gel and cream phases which are miscible relative to each other such that by rubbing and mixing a portion of the total composition together a homogeneous composition material is arrived at that can be placed directly on the subject's face or body.

Briefly, the cream phase viewed in its totality generally includes an oil, such as mineral oil, that makes up about 30-80% by weight of the entire cream phase composition. Also included in the cream phase composition is water in the amount of about 20-70% by weight, a thickening agent that makes up approximately 0.25-1.70% of the cream phase composition by weight, and an emulsifier that makes up approximately 1.0-9.0% by weight of the cream phase composition. To these basic portions of the cream phase composition, there is added in a preferred formulation a series of complimentary compositions, that is detailed in the specification which follows, and which generally includes at least one preservative, a humectant, a sequestering agent, an ultraviolet light inhibitor, color solutions, and a neutralizer for neutralizing the particular thickening agent comtemplated in the preferred embodiment.

The gel phase, on the other hand, which viewed functionally would comprise what might be considered to be an astringent or toner like composition, basically comprises water or water soluble material which makes up approximately 60-95% by weight of the gel phase composition along with a thickening agent, which may generally comprise about 0.50-2.00% by weight of the same gel phase composition. Like the cream phase, a series of complimentary compositions set forth in the specification, are added to the gel phase to complete the same.

It is, therefore, an object of the present invention to provide a multiphase cosmetic composition comprised of at least two separate, stable and visually distinct composition phases with the respective phases being continuously combined or intermixed throughout the entire formed multiphase composition.

Another object of the present invention is to provide a multi-functional cosmetic product in the form of a multiphase cosmetic composition wherein the multiphase cosmetic composition includes at least two separately functional phases.

Still a further object of the present invention is to provide a multiphase or duophase cosmetic composition in which respective phases comprising the entire composition are visibly distinct, generally stable and separately maintained, with the composition of the respective phases being such that each phase is maintained generally separately and apart from the other phase with each phase resisting migration to the other phase that could possibly yield a homogeneous cosmetic composition.

Another object of the present invention is to provide a multiphase or duophase cosmetic composition product comprised of separate and stable respective phase compositions that are formulated and composed such that the respective phases of the product remain effective, stable and distinct as originally containerized over a substantial period of time and despite the mixing and agitating effects of ordinary handling and transport.

A further object of the present invention resides in the provision of a cosmetic composition comprised of two or more phase compositions wherein two or more respective phases comprise two water miscible cosmetic admixtures.

A more particular object of the present invention is to provide a duophase cleansing cream cosmetic composition comprised of an emulsified cream phase composition and a gel phase composition with the cream phase composition generally functioning as a cleanser and wherein the respective cream and gel phase are combined in a swirl pattern continuously throughout a container to yield the duophase cleansing cream-astringent cosmetic composition.

A more particular object of the present invention resides in the provision of the duophase cleansing cream composition referred to above wherein the pH level and the viscosity of the respective phases comprising the composition and the composition itself are such that the respective phases of the multiphase composition tend to remain generally stable, separate and visually distinct.

A further object of the present invention resides in the provision of a multiphase cosmetic composition that includes utility, is functional, and yet attractive and appealing in appearance.

Other objects and advantages of the present invention will become apparent from a study of the following description and specification.

MULTIPHASE COSMETIC COMPOSITION

The present invention relates to a multiphase cosmetic composition or product comprised of at least two separate composition phases that are preferably combined in general separate phases to yield a multiphase composition or product throughout the entire product. Each respective phase of the multiphase cosmetic composition or product is formulated such that the same will remain generally stable, separate and visually distinct when viewed and considered as a part of the total composition or product. For a substantial number of cases involving multiphase compositions that are combined intimately but not blended and mixed to form a homogeneous composition, it is contemplated that each phase would be separately formulated and formed. Once formulated and formed, each respective phase could be combined during the packaging and containerization process by dispensing the respective phases simultaneously into a container, jar, or receptacle or the like in a swirl like configuration.

As noted above, it appears that in the case of producing a multiphase or duophase cosmetic composition, that it is desirable in many cases to package and containerize the product such that the respective and individual phases comprising the total product are dispensed into a container in a swirl fashion to yield a swirled or generally arcuate or circular product configuration. In accordance with the present invention, a duophase cosmetic composition is described subsequently that is of a basic cleansing cream type and which in particularly includes what is referred to as respective cream and gel phases which may generally function as a cleanser and astringent respectively. Before reviewing a detailed formulation of each phase separately, it should be pointed out that this particular cosmetic composition comprises two phases referred to as cream and gel composition phases with the cream phase being a generally water miscible cosmetic admixture and an emulsion and basically being comprised by weight of the following: an oil making up approximately 40-65% by weight or possibly as much as 30-80% by weight, water making up 35-65% or possibly as much as 20-70% by weight, a thickening agent that generally makes up approximately 0.25-3.70% by weight and an emulsifier generally making up in the range of 1.00-9.00% by weight and preferably in the range of 2.00-4.00% by weight.

In addition, to assure that the cream phase being referred to is effective, long lasting and able to withstand handling and transport and still be usable after a substantial period of time, the cream phase includes what is referred to as a series of complimentary compositions that make up the remaining portion of the cream phase by weight. This series of complimentary solutions and/or compositions could include preservatives, an ultraviolet light inhibitor, a humectant, a sequestering agent, a neutralizer, and one or more coloring solutions.

Briefly referring to the other phase of the cleansing cream composition, a gel phase is provided which may serve as a skin toner. In the gel phase, which may also be termed a water miscible cosmetic admixture, the same would basically comprise water or water soluble material that makes up generally about 60-95% by weight of the entire gel phase composition combined with a thickening agent which would generally make up about 0.50-4.00% by weight of the entire gel phase composition. Again, as in the cream phase, a series of complimentary compositions are included in the gel phase, and such may include preservatives, a sequestering agent, a neutralizer for the thickening agent, a type of emulsifier such as solulan C-24, and possibly one or more coloring agents.

Set forth below are two separate formulation tables that outline the composition or make-up of both the cream and gel phase compositions with the formulation being set forth in each table by percentage of weight for that respective phase only, and not the total combined composition that results from the two phases being combined. It is noted that in setting forth the formulation a specific formulation table is set forth, as well as is what considered to be an ideal formulation range. Finally, each table includes a major range that is contemplated for each composition or material set forth. The major ranges are thought to establish the limits of each composition or material from which an effective and feasible resultant product can be derived.

| | | CREAM PHASE FORMULATION (PERCENT BY WEIGHT OF CREAM PHASE) | | |
|---|---|---|---|---|
| MATERIAL | FURTHER DESCRIPTION WHERE APPLICABLE | MAJOR RANGE CONTEMPLATED | CONSIDERED IDEAL RANGE | AN EXAMPLE FORMULATION |
| Cleansing Oil | Mineral Oil or substitute or partial substitute including isopropyl myristate, isopropyl palmitate, decyl oleate, or isodecyl oleate | 10.00-80.00 | 40.00-65.00 | 60.000 |
| Water | | 20.00-70.00 | 25.00-50.00 | 32.796 |
| Thickening Agent | Carbomer 934 | 0.25-1.70 | 0.40-1.00 | 0.500 |
| | Carbomer 941 | 0.00-2.00 | 0.03-0.80 | 0.060 |
| Emulsifier | Polysorbate 20 | 1.00-9.00 | 2.00-4.00 | 2.400 |
| Preservative | Methyl-p-hydroxy Benzoate | 0.10-0.40 | 0.20-0.30 | 0.200 |
| | Imidazolidnyl Urea | 0.10-0.50 | 0.20-0.34 | 0.300 |
| | Propyl-p-hydroxy Benzoate | 0.05-0.40 | 0.05-0.15 | 0.050 |
| Humectant | Propylene Glycol | 0.00-15.00 | 2.00-8.00 | 3.000 |
| UV Light Inhibitor | Benzophenone-4 | 0.00-0.20 | 0.05-0.10 | 0.050 |
| Sequestering | Trisodium EDTA | 0.00-0.40 | 0.03-0.10 | 0.050 |

CREAM PHASE (continued)

| MATERIAL | FURTHER DESCRIPTION WHERE APPLICABLE | FORMULATION (PERCENT BY WEIGHT OF CREAM PHASE) | | |
|---|---|---|---|---|
| | | MAJOR RANGE CONTEMPLATED | CONSIDERED IDEAL RANGE | AN EXAMPLE FORMULATION |
| Agent | | | | |
| Color | Red No. 19 Solution | 0.001–0.50 | 0.01–0.15 | 0.073 |
| | Yellow No. 5 Solution | 0.001–0.50 | 0.01–0.15 | 0.021 |
| Neutralizer | Triethanolamine | 0.15–3.00 | 0.30–0.80 | 0.500 |
| TOTAL | | | | 100.000 |

GEL PHASE

| MATERIAL | FURTHER DESCRIPTION WHERE APPLICABLE | FORMULATION (PERCENT BY WEIGHT OF GEL PHASE) | | |
|---|---|---|---|---|
| | | MAJOR RANGE CONTEMPLATED | CONSIDERED IDEAL RANGE | AN EXAMPLE FORMULATION |
| Water or Water Soluble Material | | 50.00–99.00 | 80.00–95.00 | 90.867 |
| Thickening Agent | Carbomer 934 | 0.50–2.00 | 0.70–1.30 | 1.040 |
| | Carbomer 941 | 0.00–2.00 | 0.05–0.50 | 0.150 |
| Humectant | Propylene Glycol | 0.00–15.00 | 2.00–8.00 | 5.000 |
| Emulsifier | Choleth-24 | 0.00–5.00 | 0.50–2.00 | 1.000 |
| Preservative | Methyl-p-hydroxy Benzoate | 0.10–0.40 | 0.20–0.30 | 0.200 |
| | Propyl-p-hydroxy Benzoate | 0.05–0.40 | 0.05–0.15 | 0.050 |
| | Imidazolidnyl Urea | 0.10–0.50 | 0.20–0.35 | 0.300 |
| Color | Red No. 19 Solution | 0.001–0.50 | 0.01–0.15 | 0.065 |
| | Yellow No. 5 Solution | 0.001–0.50 | 0.01–0.15 | 0.028 |
| Neutralizer | Triethanolamine | 0.15–4.00 | 0.70–1.60 | 1.200 |
| Sequestering Agent | Trisodium EDTA | 0.00–0.40 | 0.03–0.10 | 0.050 |
| UV Light Inhibitor | Benzophenone-4 | 0.00–0.20 | 0.05–0.10 | 0.050 |
| TOTAL | | | | 100.000 |

In both the cream and gel phases referred to above, Carbomer 934 and 941 are the thickening agents used. It is believed that the use of the same thickening agent or agents in both phases tends to enhance the stability of each of the phases in the total composition and may prevent a substantial blending or unifying mixing result that might occur over a period of time which if complete would yield a more homogeneous cosmetic composition throughout as both the cream and gel phases would lose their distinctiveness. Carbomer 934 and 941 are polymers of acrylic acid cross linked with a polyfunctional agent. The thickening agents are neutralized with Triethanolamine which functions to basically neutralize the acidic state.

In both cream and gel phases, a sequestering agent, Trisodium EDTA for example is used in both phases to sequester any metal ions which may be present in the water supply. Sequestrene $Na_3T$ is a trisodium ethylene diaminetetra acidic acid.

The humectant aids in preventing drying out of the respective phase compositions and may aid in moisturizing the face. In the case of the compositions outlined above, the humectant is Propylene Glycol.

In the gel phase composition, Choleth-24 is a polymeric polyethoxylene ether of cholesterol with an average ethoxylation level of 24 moles ethylene oxide. In the gel phase composition this is used primarily to keep the parbens in solution in the product at low temperature.

In general, the pH of each phase should be within the range of 2–12 with a pH range of 5–8 being considered ideal. With respect to viscosity, a major range of 40,000–12,500,000 centipoise is contemplated for each phase. A considered ideal range for viscosity would be between 45,000–150,000 centipoise for each respective phase comprising the cleansing cream composition discussed above. In a particular formulation, the cream and gel phases were formulated and composed such that the viscosity of the cream phase was approximately 62,000 centipoise while the viscosity of the gel phase was approximately 75,000 centipoise.

In containerizing the duophase cosmetic cleansing composition referred to above, the respective phases, i.e., cream and gel phases, are formulated and composed separately, after which each is dispensed into a container, jar or other type of receptacle simultaneously. That is, both the cream and gel phases are preferably dispensed into a container simultaneously from separate dispensing heads or nozzles. Preferably the total cosmetic composition would be made up of about 2½–3 parts gel to 1 part cream. However, the total composition could include generally 40–90% gel by weight, and generally 10–60% cream by weight. In addition, it is preferable that the respective cream and gel phases be combined or intimately contained within a container in a swirl or marble like configuration. This is achieved by the provision of relative rotational movement between the containers and the dual dispensing head and with the filling apparatus so adjusted that there is also relative vertical movement between the container and the dual filling head such that the container can be filled from bottom to top.

Generally respective swirls of any one phase can vary from about 1/16 inch by 1/16 inch to generally one inch in diameter and extending around the entire jar or container.

From the foregoing specification, it is apparent that the present invention presents a multiphase cosmetic composition that is functional and also appealing and attractive in appearance. In the case of the duophase cleansing cream-astringent type composition disclosed herein, it is appreciated that both the cream and gel phases comprising the entire composition are formulated and composed so as to remain generally stable, separate and visually distinct over a substantial period of time and despite the agitating and mixing action that might result from handling and transport. It should be noted that in the case of the duophase cleansing composition just referred to, that the cream phase generally functions as a cleanser while the gel phase may serve as an astringent. The cleanser functions primarily by emulsifying dirt on the face into the entire product itself so that the dirt or make-up on the face is removed along with the cleanser when the cleanser is tissued or rinsed from the face.

The present invention, of course, may be carried out in other specific ways than those herein set forth without departing from the spirit and essential characteristics of the invention. The present embodiments are, therefore, to be considered in all respects as illustrative and not restrictive, and all changes coming within the meaning and equivalency range are intended to be embraced herein.

What is claimed is:

1. A multiphase cosmetic composition comprising two generally separately stable and visual distinct gel and cream phases combined to form a cosmetic composition; said cream phase being an emulsified composition and including an emulsifier, a thickening agent, an oil phase, and water, with the oil phase making up generally 10-80% by weight of said cream phase and the water making up generally 20-70% by weight of said cream phase; said gel phase including a thickening agent and a phase including water soluble material ranging from 50-99% by weight of said gel phase; and wherein said cream and gel phases are disposed side by side throughout the multiphase cosmetic composition formed by said cream and gel phases.

2. The multiphase cosmetic composition of claim 1 wherein said thickening agents utilized in both said cream and gel phases are substantially alike in composition.

3. The multiphase cosmetic composition of claim 2 wherein both said cream and gel phases include a neutralizing solution for neutralizing the substantially alike thickening agents included in both said cream and gel phases.

4. The multiphase cosmetic composition of claim 1 wherein the thickening agent included in both said cream and gel phases includes Carbomer 934.

5. The multiphase cosmetic composition of claim 4 wherein the Carbomer thickening agent in said cream phase comprises at least 0.25% by weight of said cream phase composition, and wherein the Carbomer thickening agent in said gel phase comprises at least 0.50% by weight of said gel phase composition.

6. The cosmetic composition of claim 1 wherein the cosmetic composition formed by said cream and gel phases falls within a pH range of 5-8.

7. The cosmetic composition of claim 1 wherein the viscosity of both said cream and gel phases range between 40,000 to 150,000 centipoise.

8. The cosmetic composition of claim 1 wherein the emulsifier included in the cream phase makes up at least 2.00% by weight of the total weight of said cream phase.

9. The cosmetic composition of claim 8 wherein said emulsifier is Polysorbate 20.

10. A duophase cleansing cream composition including two generally separate and stable composition phases intimately combined to yield a cleanser type cosmetic composition that may be applied to the subject's face or body in one single application, said duophase cleansing cream composition comprising: a water miscible cleansing cream phase composition having a pH in the range of 5-8 and a viscosity of 40,000 to 150,000 centipoise and wherein said cream phase composition itself includes an oil phase making up about 40-65% by weight of the cream phase composition, water making up about 20-50% by weight of the cream phase composition, a thickening agent making up about 0.25-1.70% by weight of the cleansing cream composition, and an emulsifier making up about 1.00 to 9.00% by weight of the cleansing cream composition; a water miscible gel phase composition having a pH in the range of 5-8 and a viscosity of 40,000 to 150,000 centipoise and wherein said gel phase composition itself includes water which makes up about 80-90% by weight of the gel phase composition, and a thickening agent making up about 0.50-4.00% by weight of said gel phase composition; and wherein said cream phase composition and said gel phase composition are intimately combined throughout to form a continuous duophase cosmetic composition with the cream and gel phases remaining generally stable, separate, and visually distinct relative to each other but combined in a swirl like pattern such that the cream and gel phases occur and are present throughout the total formed duophase composition.

11. The duophase cosmetic cleansing cream composition of claim 10 wherein the thickening agent used in both said cream and gel phases is substantially identical in composition and make-up.

12. The duophase cosmetic cleansing cream of claim 11 wherein each of the cream and gel phase compositions includes a complimentary make-up of at least one preservative, a neutralizer for neutralizing the thickening agent in each phase, and a humectant; and wherein in said cream phase said preservative comprises about 0.25-1.30% by weight, said neutralizer comprises about 0.15-3.00% by weight, and said humectant comprises about 2.00-8.00% by weight; and wherein in the gel phase composition, said preservative comprises about 0.25-1.30% by weight, said neutralizer comprises about 0.15-4.00% by weight, and said humectant comprises about 2.00-8.00% by weight, with the respective percentage weights being set forth relative to their respective phase compositions.

13. The duophase cosmetic cleansing cream composition of claim 10 wherein said cream phase composition further includes the following with each being expressed as a percentage of weight of said cream phase composition itself: at least one preservative with the total preservative make-up of the cream phase composition being about 0.25-1.30% by weight of said cream phase composition; at least one color solution with the total color solution make-up of said cream phase composition being about 0.001-1.00% by weight; a humectant being 2.00-8.00% by weight of said cream phase composition; a neutralizer for neutralizing said thickening agent including about 0.15-3.00% by weight of said cream phase composition; a sequestering agent being about 0.03–0.10% by weight of said cream phase composition; and an ultraviolet light inhibitor being approximately 0.05–0.10% by weight of the cream phase composition; and wherein said gel phase composition further includes the following with each being expressed as a percentage of weight of said gel phase composition: at least one preservative with the total preservative makeup of said gel phase composition being approximately 0.25–1.30% by weight; a humectant being approximately 2.00–8.00% by weight of said gel phase composition, a coloring solution including at least one coloring agent being about 0.001–0.50% by weight of the gel phase composition, a neutralizing agent for neutralizing said thickening agent therein with the neutralizing agent being about 0.15–4.00% by weight of said gel phase composition; a sequestering agent being about 0.03–0.40% by weight of said gel phase composition; and an ultraviolet light inhibitor being approximately 0.05–0.10% by weight of said gel phase composition.

14. The duophase cosmetic cleansing cream composition of claim 10 wherein said thickening agent included in both said cream and gel phases include Carbomer 934 with the Carbomer 934 in the cream phase being approximately 0.25–1.70% by weight of the cream phase composition, and wherein the Carbomer 934 in said gel phase is approximately 0.50–2.00% by weight of the gel phase itself.

15. The duophase cleansing cream composition of claim 14 wherein said emulsifier in said cream phase is Polysorbate 20 and wherein the percentage by weight of said emulsifier in said cream phase composition is approximately 2.00–4.00% by weight.

* * * * *